United States Patent
Kita et al.

(10) Patent No.: US 9,790,165 B2
(45) Date of Patent: Oct. 17, 2017

(54) PRODUCTION PROCESS AND PURIFICATION PROCESS OF 4-HYDROXY-BENZOIC ACID LONG CHAIN ESTER

(71) Applicant: UENO FINE CHEMICALS INDUSTRY, LTD., Osaka-shi, Osaka (JP)

(72) Inventors: Yusuke Kita, Sanda (JP); Toshihide Komatsu, Kobe (JP); Takaya Hisano, Takarazuka (JP); Kuniyo Yanagawase, Sanda (JP); Mio Tsuchiya, Sanda (JP)

(73) Assignee: UENO FINE CHEMICALS INDUSTRY, LTD., Osaka (JP)

( * ) Notice: Subject to any disclaimer, the term of this patent is extended or adjusted under 35 U.S.C. 154(b) by 0 days.

(21) Appl. No.: 15/130,180

(22) Filed: Apr. 15, 2016

(65) Prior Publication Data
US 2016/0318841 A1    Nov. 3, 2016

(30) Foreign Application Priority Data

| Apr. 30, 2015 | (JP) | 2015-093389 |
| Apr. 30, 2015 | (JP) | 2015-093393 |
| May 27, 2015 | (JP) | 2015-107751 |
| May 27, 2015 | (JP) | 2015-107753 |
| Nov. 26, 2015 | (JP) | 2015-230427 |
| Feb. 25, 2016 | (JP) | 2016-034199 |

(51) Int. Cl.
*C07C 69/88* (2006.01)
*C07C 67/28* (2006.01)
*C07C 67/03* (2006.01)
*C07C 67/58* (2006.01)
*C07C 67/52* (2006.01)

(52) U.S. Cl.
CPC .............. *C07C 67/28* (2013.01); *C07C 67/03* (2013.01); *C07C 67/52* (2013.01); *C07C 67/58* (2013.01)

(58) Field of Classification Search
CPC .......... C07C 67/58; C07C 69/84; C07C 67/03; C07C 67/28; C07C 67/52; C07C 67/31; C07C 67/62; C07C 69/76; B01J 21/063; B01J 21/066; B01J 23/14; B01J 23/18
See application file for complete search history.

(56) References Cited

U.S. PATENT DOCUMENTS 5,426,212 A * 6/1995 Kim ................... C07C 67/03
                                              560/67
5,648,483 A * 7/1997 Granberg ............ C07C 67/03
                                              536/115

FOREIGN PATENT DOCUMENTS

JP    2014-108928 A    6/2014

OTHER PUBLICATIONS

Dymicky et al. (Inhibition of Clostridium botulinum by p-Hydroxybenzoic Acid n-Alkyl Esters, Antimicrobial Agents and Chemotherapy, p. 798-801, published Jun. 1979).*
Chen et al. (Nucleophilic Acyl Substitutions of Esters with Protic Nucleophiles Mediated by Amphoteric, Oxotitanium, and Vanadyl Species, J. Org. Chem., 70, 1328-1339, Published 2005).*
Communication dated Sep. 1, 2016, issued by the European Patent Office in corresponding European Application No. 16166386.9.
K. Vosmann et al., "Preparation of lipophilic alkyl (hydroxy)benzoates by solvent-free lipase-catalyzed esterification and transesterification", Appl Microbiol Biotechnol (2008), vol. 80, pp. 29-36.

* cited by examiner

*Primary Examiner* — Yevegeny Valenrod
*Assistant Examiner* — Blaine G Doletski
(74) *Attorney, Agent, or Firm* — Sughrue Mion, PLLC

(57) ABSTRACT

The present invention relates to a production process of a 4-hydroxy-benzoic acid long chain ester, that includes a step of reacting a 4-hydroxy-benzoic acid short chain ester with an aliphatic alcohol in the presence of a metal catalyst. The present invention also relates to a purification process of a 4-hydroxy-benzoic acid long chain ester, that includes a step of adding an acid aqueous solution to a crude composition including the 4-hydroxy-benzoic acid long chain ester, separating the crude composition to an organic phase and a water phase and extracting the organic phase.

24 Claims, No Drawings

PRODUCTION PROCESS AND PURIFICATION PROCESS OF 4-HYDROXY-BENZOIC ACID LONG CHAIN ESTER

TECHNICAL FIELD

This patent application claims the benefit of Japanese Patent Application No. 2015-093389 (filed on Apr. 30, 2015), Japanese Patent Application No. 2015-107751 (filed on May 27, 2015), Japanese Patent Application No. 2015-107753 (filed on May 27, 2015), Japanese Patent Application No. 2015-093393 (filed on Apr. 30, 2015), Japanese Patent Application No. 2015-230427 (filed on Nov. 26, 2015), and Japanese Patent Application No. 2016-034199 (filed on Feb. 25, 2016), the entirety of which is incorporated herein by reference.

The present invention relates to a production process of a 4-hydroxy-benzoic acid long chain ester and a purification process of the 4-hydroxy-benzoic acid long chain ester.

BACKGROUND ART

The 4-hydroxy-benzoic acid long chain ester has a structure having a hydroxyl group and a hydrophobic group. On the basis of the structural feature thereof, the uses for a plasticizing agent, a compatibilizing agent, a surface active agent, and the like have been proposed.

As to esterification of a compound, a production process of an ester in which a carboxylic acid and an alcohol as the raw materials are reacted in the presence of a protic acid catalyst such as sulfuric acid; the catalyst and the unreacted carboxylic acid are removed from the resulting reaction liquid; and, if necessary, purification such as crystallization or distillation is conducted is known (Patent Document 1).

As to also esterification of 4-hydroxy-benzoic acid, it is known that a 4-hydroxy-benzoic acid short chain ester is relatively easily obtained by a reaction of 4-hydroxy-benzoic acid with a short chain alcohol having 1 to 6 carbon atom(s).

In a reaction of 4-hydroxy-benzoic acid with a long chain alcohol having 16 or more carbon atoms to obtain a 4-hydroxy-benzoic acid long chain ester, when the acid and the alcohol are similarly reacted in the presence of a protic acid catalyst, however, the generation of a side product such as an ether generated by dimerization of the long chain alcohol and a sulfate ester generated by a reaction of the long chain alcohol with the protic acid catalyst is inevitable.

The side products have physical properties similar to those of the 4-hydroxy-benzoic acid long chain ester which is the target substance, and are therefore difficult to be removed using crystallization or distilling. Therefore, no 4-hydroxy-benzoic acid long chain ester of high purity can be obtained.

When the scale increases, in general, the reactivity is degraded and the yield of the target substance is reduced. Therefore, a production process in which a 4-hydroxy-benzoic acid long chain ester can be obtained at a substantially equal yield even when the scale increases has been sought.

On the other hand, purification is generally conducted by extraction using water or alkali water after melting a crude crystal which ordinarily includes the target substance or after dilution using a non-aqueous solvent. As to a crude composition of the 4-hydroxy-benzoic acid long chain ester containing impurities such as the unreacted carboxylic acid and the catalyst, however, even when extraction is attempted by adding water or alkali water, the extraction is difficult because the liquid separation property thereof is extremely low. Even when the extraction is conducted, the yield and the purity are low and no target substance of high purity can be obtained.

Patent Document 1: Japanese Patent Publication No. 2014-108928

SUMMARY OF THE INVENTION

An object of the invention is to provide a production process of a 4-hydroxy-benzoic acid long chain ester, in which generation of any side product is suppressed.

Another object of the invention is to provide a production process in which a 4-hydroxy-benzoic acid long chain ester of high purity can be obtained.

Yet another object of the invention is to provide a purification process in which residual substances such as a catalyst and reaction raw materials can easily be removed from a crude composition containing a 4-hydroxy-benzoic acid long chain ester (hereinafter, also referred to as "crude composition") and in which a 4-hydroxy-benzoic acid long chain ester of high purity can be obtained.

The inventors actively studied a production process of a 4-hydroxy-benzoic acid long chain ester. As a result, the inventors found that generation of any side product can be suppressed and a 4-hydroxy-benzoic acid long chain ester of high purity can be obtained by conducting a so-called transesterification reaction between a 4-hydroxy-benzoic acid short chain ester and a long chain alcohol using a metal catalyst as the catalyst. The inventors thereby completed the invention.

The inventors also found that, as to a transesterification reaction, a 4-hydroxy-benzoic acid long chain ester can be obtained at a high yield regardless of the scale of the reaction container and the volume of the reaction system, by conducting the transesterification reaction while a predetermined amount of an inert gas is flowed into the reaction system. The inventors thereby completed the invention.

Furthermore, the inventors actively studied a purification process of a 4-hydroxy-benzoic acid long chain ester. As a result, the inventors found that an unreacted carboxylic acid, a catalyst and the like can be removed by adding an acid aqueous solution to a crude composition containing a 4-hydroxy-benzoic acid long chain ester, separating the crude composition to an organic phase and a water phase and extracting the organic phase. The inventors thereby completed the invention.

The present invention, in one gist thereof, provides a production process of a 4-hydroxy-benzoic acid long chain ester represented by formula (3), which comprises a step of reacting a 4-hydroxy-benzoic acid short chain ester represented by formula (1) with an aliphatic alcohol represented by formula (2) in the presence of a metal catalyst.

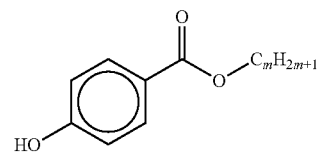

(1)

(2)

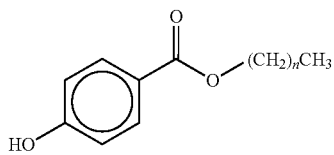

(3)

(wherein "m" represents an integer from 1 to 11 and "n" represents an integer from 15 to 23.)

The present invention, in another aspect thereof, provides the production process which comprises a step of reacting the 4-hydroxy-benzoic acid short chain ester with the aliphatic alcohol under a gas flow of an inert gas of 0.10 to 0.50 mL/min per 1 g of the total amount of the 4-hydroxy-benzoic acid short chain ester and the aliphatic alcohol in the above reaction.

The present invention, in a preferred aspect thereof, provides the production process which further comprises a step of adding the acid aqueous solution to the crude composition containing the 4-hydroxy-benzoic acid long chain ester represented by formula (3), separating the crude composition to an organic phase and a water phase and extracting the organic phase.

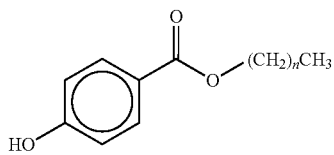

(3)

(wherein "n" represents an integer from 15 to 23.)

The present invention, in another gist thereof, provides a purification process of a 4-hydroxy-benzoic acid long chain ester, which comprises a step of adding an acid aqueous solution to a crude composition containing a 4-hydroxy-benzoic acid long chain ester represented by formula (3), separating the crude composition to an organic phase and a water phase and extracting the organic phase.

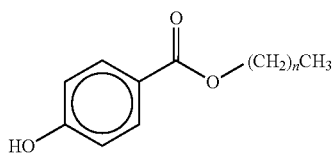

(3)

(wherein "n" represents an integer from 15 to 23.)

The present invention, in a preferred gist thereof, provides a production process of a 4-hydroxy-benzoic acid long chain ester represented by formula (3), which comprises a step of obtaining a crude composition containing the 4-hydroxy-benzoic acid long chain ester represented by formula (3) by reacting a 4-hydroxy-benzoic acid short chain ester represented by formula (1) and an aliphatic alcohol represented by formula (2) in the presence of a metal catalyst, and a step of adding an acid aqueous solution to the crude composition, separating the crude composition to an organic phase and a water phase and extracting the organic phase.

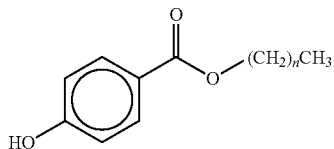

(1)

$CH_3(CH_2)_nOH$ (2)

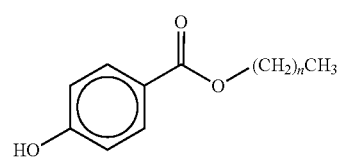

(3)

(wherein "m" represents an integer from 1 to 11 and "n" represents an integer from 15 to 23.)

Effects of the Invention

A 4-hydroxy-benzoic acid long chain ester of high purity can be obtained by suppressing generation of any side products such as an ester generated by dimerization of a long chain alcohol and a sulfate ether generated by a reaction of a long chain alcohol with a catalyst which are by-generated in an ordinary esterification reaction, by including in the process a step of reacting a 4-hydroxy-benzoic acid short chain ester and an aliphatic alcohol in the presence of a metal catalyst. The 4-hydroxy-benzoic acid long chain ester of higher purity can be obtained by using a simple process without conducting any complicated purification by, preferably, adding an acid aqueous solution to a crude composition including a 4-hydroxy-benzoic acid long chain ester, separating the crude composition to an organic phase and a water phase and extracting the organic phase.

According to the production process of the invention, even when the scale is industrially increased, the reactivity is not degraded and a 4-hydroxy-benzoic acid long chain ester can be obtained at a high yield by reacting a 4-hydroxy-benzoic acid short chain ester with an aliphatic alcohol under a gas flow of an inert gas of 0.10 to 0.50 mL/min per 1 g of the total amount of a 4-hydroxy-benzoic acid short chain ester and an aliphatic alcohol in the above reaction.

According to the purification process of the invention, a 4-hydroxy-benzoic acid long chain ester of higher purity can be obtained because an unreacted carboxylic acid, a catalyst and the like can efficiently be removed by adding an acid aqueous solution to a crude composition containing a 4-hydroxy-benzoic acid long chain ester, separating the crude composition to an organic phase and a water phase and extracting the organic phase.

EMBODIMENTS OF THE INVENTION

In a production process of a 4-hydroxy-benzoic acid long chain ester represented by formula (3), a 4-hydroxy-benzoic acid short chain ester represented by formula (1) to be a starting material is an ester made of 4-hydroxy-benzoic acid and an alcohol which has 1 to 11 carbon atom(s) and may have a linear chain or a branch.

Specific examples of the 4-hydroxy-benzoic acid short chain ester represented by formula (1) include methyl 4-hydroxy-benzoate, ethyl 4-hydroxy-benzoate, propyl 4-hydroxy-benzoate, isopropyl 4-hydroxy-benzoate, butyl 4-hydroxy-benzoate, isobutyl 4-hydroxy-benzoate, pentyl 4-hydroxy-benzoate, hexyl 4-hydroxy-benzoate, heptyl 4-hydroxy-benzoate, octyl 4-hydroxy-benzoate, nonyl 4-hydroxy-benzoate, decyl 4-hydroxy-benzoate, undecyl 4-hydroxy-benzoate, ethylhexyl 4-hydroxy-benzoate, and the like.

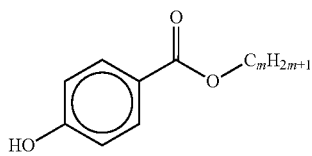

(1)

(wherein "m" represents an integer from 1 to 11.)

Among the above, preferably, methyl 4-hydroxy-benzoate, ethyl 4-hydroxy-benzoate, propyl 4-hydroxy-benzoate, isopropyl 4-hydroxy-benzoate, butyl 4-hydroxy-benzoate, and/or isobutyl 4-hydroxy-benzoate may be used based on the point that these esters are excellent in the easy availability and the reactivity. More preferably, methyl 4-hydroxy-benzoate may be used based on the point that this ester is especially excellent in the reactivity.

Any commercially available 4-hydroxy-benzoic acid short chain ester may be used as a 4-hydroxy-benzoic acid short chain ester, and any 4-hydroxy-benzoic acid short chain ester may be used that is obtained by an ordinary esterification reaction to react a 4-hydroxy-benzoic acid with an aliphatic alcohol having 1 to 11 carbon atom(s) in the presence of a protic acid catalyst.

The aliphatic alcohol is an aliphatic alcohol having 16 to 24 carbon atoms and represented by $$CH_3(CH_2)_nOH \quad (2)$$

(wherein "n" represents an integer from 15 to 23). Specific examples of the aliphatic alcohol include one or more selected from the group consisting of hexadecanol, heptadecanol, octadecanol, nonadecanol, icosanol, henicosanol, docosanol, tricosanol, and tetracosanol.

Any commercially available aliphatic alcohol may be used as an aliphatic alcohol, or an aliphatic alcohol produced using a process known among those in the art may be used.

The aliphatic alcohol may be reacted in an amount of 0.1 to 3 mol, preferably 0.5 to 1.5 mol, more preferably 0.8 to 1.2 mol, especially preferably 0.9 to 0.98 mol relative to 1 mol of the 4-hydroxy-benzoic acid short chain ester.

When the amount of the aliphatic alcohol is smaller than 0.1 mol relative to 1 mol of the 4-hydroxy-benzoic acid short chain ester, the sub-generation reaction tends to easily take place and the 4-hydroxy-benzoic acid short chain ester becomes excessive resulting in waste of the raw material. When the amount of the aliphatic alcohol is larger than 3 mol relative thereto, an excessive amount of aliphatic alcohol remains and the purity of the ester tends to be degraded.

In the reaction of the 4-hydroxy-benzoic acid short chain ester with the aliphatic alcohol having 16 to 24 carbon atoms, generation of side products such as an ether generated by dimerization of the long chain alcohol and a sulfate ester generated by a reaction of the long chain alcohol with a catalyst can be suppressed and the 4-hydroxy-benzoic acid long chain ester of high purity can be obtained by causing a metal catalyst to be present therein.

Examples of the metal catalyst include one or more selected from the group consisting of a titanium-based catalyst, a tin-based catalyst, an antimony-based catalyst, and a zirconium-based catalyst. The titanium-based catalyst may be advantageously used based on the point that this catalyst is excellent in the easy availability and the reactivity.

Specific examples of the titanium-based catalyst include titanium tetramethoxide, titanium tetraethoxide, titanium tetra-n-propoxide, titanium tetraisopropoxide, titanium tetra-n-butoxide, titanium tetraisobutoxide, titanium tetra-2-ethylhexoxide, and titanium tetraoctadecoxide. Preferably, titanium tetraisopropoxide may be used based on the point that this catalyst is excellent in the reactivity and the easy availability.

Specific examples of the tin-based catalyst include monobutyl-tin oxide, dibutyl-tin oxide, dibutyl-tin laurate, dioctyl-tin laurate, and dibutyldiisopropoxy-tin. Monobutyl-tin oxide and dibutyl-tin oxide are preferable based on the point that these catalysts are excellent in the reactivity and the easy availability.

Specific examples of the antimony-based catalyst include antimony acetate, antimony trioxide, diantimony pentoxide, trimethoxy-antimony, triethoxy-antimony, tri-n-propoxy-antimony, triphenyl-antimony. Preferably, antimony acetate may be used based on the point that this catalyst is excellent in the reactivity and the easy availability.

Specific examples of the zirconium-based catalyst include zirconium tetramethoxide, zirconium tetraethoxide, zirconium tetra-n-propoxide, zirconium tetraisopropoxide, zirconium tetra-n-butoxide, zirconium tetraisobutoxide, zirconium tetra-2-ethylhexoxide, zirconium tetraoctadecoxide, and zirconium acetate oxide. Preferably, zirconium tetra-n-butoxide may be used based on the point that this catalyst is excellent in the reactivity and the easy availability.

Each of these catalysts may be used alone or two or more thereof may be used in combination.

The amount of the metal catalyst advantageously may be 0.1 to 10 part(s) by weight, preferably 0.5 to 7 parts by weight, and, more preferably 1 to 5 part(s) by weight relative to 100 parts by weight of the 4-hydroxy-benzoic acid short chain ester.

When the amount of the metal catalyst is smaller than 0.1 parts by weight relative to 100 parts by weight of the 4-hydroxy-benzoic acid short chain ester, the reaction tends to insufficiently take place. When the amount of the metal catalyst is larger than 10 parts by weight relative thereto, side products such as a dimerized ester of the aliphatic alcohol tend to be generated and the economic efficiency is degraded.

The reaction of the 4-hydroxy-benzoic acid short chain ester with the aliphatic alcohol having 16 to 24 carbon atoms may be conducted at, preferably a temperature from 120 to 200° C. and at, more preferably a temperature from 150 to 180° C. When the reaction temperature is lower than 120° C., the reaction tends to insufficiently take place and, when the reaction temperature is higher than 200° C., the side products tend to be generated and an energy loss occurs.

The reaction time period is not especially limited because the time period is varied depending on the conditions such as the reaction temperature. The reaction time period may be properly selected between 1 to 20 hour(s), preferably between 3 to 15 hours, and more preferably between 5 to 10 hours.

The reaction of the 4-hydroxy-benzoic acid short chain ester with the aliphatic alcohol having 16 to 24 carbon atoms may be conducted under a gas flow of an inert gas of 0.10 to 0.50 mL/min per 1 g of the total amount of the 4-hydroxy-benzoic acid short chain ester and the aliphatic alcohol.

The inert gas may only be a gas which does not obstruct the reaction of the 4-hydroxy-benzoic acid short chain ester with the aliphatic alcohol. Specific examples thereof include one or more selected from the group consisting of nitrogen, carbon dioxide, argon, helium, neon, xenon, and krypton. Among them, preferably, nitrogen may be used based on the point that nitrogen is excellent in the easy availability and the economic efficiency.

The flow of the inert gas in the reaction system advantageously may be, preferably 0.15 to 0.45 mL/min and, more preferably 0.20 to 0.40 mL/min. When the flow of the inert gas is smaller than 0.10 mL/min, the reactivity tends to be degraded. When the flow is larger than 0.50 mL/min, the generation of the side products tends to be enhanced. The reaction can more efficiently be conducted by adjusting the flow of the inert gas corresponding to the total amount of the 4-hydroxy-benzoic acid short chain ester and the aliphatic alcohol.

The inert gas may be blown into a space above the reaction liquid in the reaction container accommodating the 4-hydroxy-benzoic acid short chain ester and the aliphatic alcohol which are the raw materials, or the inert gas may directly be blown into the reaction liquid.

The reaction may be conducted in the presence of the inert gas of the proper flow rate using a reaction container of a small scale or even using a reaction equipment of an industrially increased scale, by setting the flow rate of the inert gas to be blown into the reaction system relative to the total amount (g) of the 4-hydroxy-benzoic acid short chain ester and the aliphatic alcohol which are reaction raw material.

Even when the volume of the reaction container or the scale of the reaction system is varied, the reactivity is not degraded and the 4-hydroxy-benzoic acid long chain ester can be obtained at a high yield.

In the step of reacting the 4-hydroxy-benzoic acid short chain ester represented by formula (1) with the aliphatic alcohol represented by formula (2) in the presence of the metal catalyst, the degree of purity of the resulting crude composition including the 4-hydroxy-benzoic acid long chain ester represented by formula (3) may be increased using a purification step or a purification process. The purification step or the purification process includes a step of adding an acid aqueous solution to the crude composition, separating an organic phase and a water phase and extracting the organic phase.

The crude composition including the 4-hydroxy-benzoic acid long chain ester represented by formula (3) means a composition which contains impurities such as the reaction raw materials, the catalyst and the reaction side products in addition to the 4-hydroxy-benzoic acid long chain ester represented by formula (3) which is the target substance. The content of the impurities also differs depending on the reaction process. The content of the impurities is usually 1 to 20% by weight, preferably 3 to 10% by weight in the crude composition.

The crude composition containing the 4-hydroxy-benzoic acid long chain ester represented by formula (3) may be a crude composition obtained in the step of reacting the 4-hydroxy-benzoic acid short chain ester represented by formula (1) with the aliphatic alcohol represented by formula (2) in the presence of the metal catalyst or may be a crude composition which contains the 4-hydroxy-benzoic acid long chain ester represented by formula (3) and which is commercially available.

Examples of the 4-hydroxy-benzoic acid long chain ester represented by formula (3) to be the target substance include one or more selected from hexadecyl 4-hydroxy-benzoate, heptadecyl 4-hydroxy-benzoate, octadecyl 4-hydroxy-benzoate, nonadecyl 4-hydroxy-benzoate, icosyl 4-hydroxy-benzoate, henicosyl 4-hydroxy-benzoate, docosyl 4-hydroxy-benzoate, tricosyl 4-hydroxy-benzoate, and tetracosyl 4-hydroxy-benzoate. Among these, preferably, hexadecyl 4-hydroxy-benzoate is used.

Examples of the impurities contained in the crude composition include residues of the raw material such as 4-hydroxy-benzoic acid and the catalyst, and the like. The impurities also include the reaction side products such as a dimerized ester of the long chain alcohol, a sulfate ester generated by the reaction of the long chain alcohol with the protic acid catalyst, and the like.

In the step of extracting the organic phase after adding the acid aqueous solution to the crude composition to establish separation of the organic phase and the water phase (hereinafter, referred to as "extraction step"), for example, after the acid aqueous solution is added to the crude composition, the mixture is heated being stirred to melt the organic substances in the crude composition, and the catalyst is deactivated by continuing the stirring. The reaction system is thereafter left untouched to establish the separation of an organic phase and a water phase, and the organic phase is collected.

Preferably, the solvent used in the acid aqueous solution at the extraction step is a mixture of water and a lower alcohol. Examples of the lower alcohol include one or more selected from the group consisting of methanol, ethanol, 1-propanol, and 2-propanol. Among these, preferably, methanol is used based on the point that methanol is excellent in the yield and the economic efficiency.

The ratio by weight of the water and the lower alcohol (water/the lower alcohol) may be varied depending on the type of the used alcohol. Therefore, the ratio by weight of the water and the lower alcohol is not especially limited. The ratio by weight of the water and the lower alcohol is advantageously 5/5 to 2/8, preferably 4/6 to 2/8.

When the ratio by weight of water and the lower alcohol is greater than 5/5, the crude composition and the acid aqueous solution tend to be emulsified and the catalyst tends to be unable to sufficiently be removed. When the ratio by weight of water and the lower alcohol is smaller, than 2/8, the overall reaction system becomes a homogeneous solution and the catalyst therefore tends also to be unable to sufficiently be removed.

The acid used in the acid aqueous solution is an acid which deactivates the catalyst and examples of the acid include one or more selected from the group consisting of, for example, hydrochloric acid, sulfuric acid, nitric acid, phosphoric acid, acetic acid, carboxylic acid, and sulfonic acid. Among these, preferably, phosphoric acid is used based on the point that the color tone of the resulting 4-hydroxy-benzoic acid long chain ester is improved.

As to the amount of the acid used in the acid aqueous solution, the amount of the acid is advantageously 0.1 to 10% by weight, preferably 0.5 to 8% by weight, and more preferably 1 to 5% by weight relative to that of the solvent.

When the amount of the acid is smaller than 0.1% by weight relative to that of the solvent, the catalyst tends to be unable to sufficiently be removed. When the amount of the acid is larger than 10% by weight relative thereto, the acid tends to remain as an impurity.

The amount of the acid aqueous solution advantageously may be a 1-fold amount by weight or larger, preferably a 2-fold amount by weight or larger, and more preferably a four-fold amount by weight or larger relative to the weight of the crude composition. When the amount of the acid aqueous solution is smaller than the 1-fold amount by weight relative thereto, the liquid separation property of the organic phase and the water phase tends to be degraded and the catalyst tends to be unable to sufficiently be removed.

In the extraction step, the reaction system is heated to a temperature of 50° C. or higher and, preferably of 60° C. or higher to melt the organic substances in the reaction system. The stirring is continued at this temperature to deactivate the catalyst. Next, the reaction system is left untouched until the organic phase and the water phase are separated from each other. After that, the separated organic phase is collected.

Preferably, the organic phase collected at the extraction step is crystalized at a crystallization step. In the crystallization step, an organic solvent is added to the organic phase. The mixture is heated to be melted. The mixture is thereafter cooled to thereby be able to crystalize the target substance. Solid-liquid separation is conducted for the precipitated crystals using filtering and the like. The crystals are washed and are dried. After that, the 4-hydroxy-benzoic acid long chain ester of high purity can thereby be obtained.

Examples of the organic solvent used in the crystallization step include alcohols such as methanol, ethanol, 1-propanol, 2-propanol, and ethyleneglycol, ketones such as acetone, methylethylketone, and methylisobutylketone, esters such as methyl acetate, ethyl acetate, propyl acetate, and butyl acetate, amide-based compounds such as N,N'-dimethylformamide, N-methylpyrolidone, and pyridine, hydrocarbon-series compounds such as pentane, hexane, heptane, benzene, toluene, xylene, and cyclohexane, organic halogens such as chloroform and dichloromethane, and ethers such as diisopropyl ether, tetrahydrofuran, and 1,4-dioxane. Among these, preferably, methanol, ethanol, 1-propanol, 2-propanol, acetone, methylethylketone, methylisobutylketone, methyl acetate, ethyl acetate, propyl acetate, hexane, heptane, toluene, and xylene are used based on the point that these solvents are excellent in the easy availability and the industrial productivity such as the drying efficiency and, especially preferably, methanol is used based on the point that methanol is excellent in the yield.

The amount of the organic solvent used at the crystallization step is varied depending on the type of the used solvent and is therefore not especially limited. The amount is advantageously a 1-fold amount to a 20-fold amount by weight, preferably a 1.5-fold amount to a 10-fold amount by weight, and more preferably a 2.5-fold amount to a 5-fold amount by weight relative to the weight of the crude composition.

When the amount of the organic solvent is smaller than a 1-fold amount by weight relative thereto, poor stirring tends to occur during the crystallization. When the amount is larger than a 20-fold amount by weight relative thereto, the yield tends to be reduced and economic disadvantage occurs.

In the crystallization step, after the organic solvent is added, the reaction system is heated to completely dissolve the organic substances in the organic phase. After that, the stirring is thereafter continued cooling slowly the reaction system to crystalize.

When a supersaturation phenomenon occurs during the crystallization, the crystallization may be urged by properly adding a seed crystal.

Solid-liquid separation is conducted for the crystals precipitated at the crystallization step using a usual process such as filtering to collect the 4-hydroxy-benzoic acid long chain ester which is the target substance. Preferably, during the solid-liquid separation, the crystals are washed pouring properly the organic solvent thereon. The same organic solvent as the organic solvent used at the crystallization step is used in the solid-liquid separation.

The crystals collected by the solid-liquid separation are dried they are as crystals under a reduced pressure and at a temperature of 50° C. or lower, or the crystals are heated to 50° C. or higher to melt the crystals. After that, the solvent is thereafter removed. The 4-hydroxy-benzoic acid long chain ester of high purity can thereby be acquired.

Purification process A to C as below may be conducted in the purification process or in the purification step. The purification process or the purification step is properly selected depending on the amount of the impurities contained in the crude composition containing the 4-hydroxy-benzoic acid long chain ester represented by formula (3), the quality of the 4-hydroxy-benzoic acid long chain ester required after the purification, and the like. The purification process may each be used alone or may be used in combination.

[Purification Method A]

In the purification process A, at a melting step, the crude composition of the 4-hydroxy-benzoic acid long chain ester is first melted. In the melting step, the crude composition of the 4-hydroxy-benzoic acid long chain ester is heated to the melting point thereof or a higher temperature. The temperature of the meltage of the crude composition of the 4-hydroxy-benzoic acid long chain ester (hereinafter, also referred to as "melted crude composition") is not especially limited as far as the melted state is maintained while, preferably, the temperature is 90 to 110° C.

A crystal precipitation step is applied to the melted crude composition. The crude composition containing the 4-hydroxy-benzoic acid long chain ester is obtained in its melted state from the reaction of the 4-hydroxy-benzoic acid with the aliphatic alcohol. After the reaction is completed, therefore, the crude composition whose temperature is maintained in a temperature range within which the melted state is maintained may be used as it is as the melted crude composition in the crystal precipitation step.

At the crystal precipitation step, the melted crude composition is added to an organic solution whose temperature is maintained at a temperature lower than 45° C., preferably at 5 to 42° C. while stirring, to precipitate the crystals.

Preferably, the organic solution used at the crystal precipitation step is a mixture of water and an aqueous organic solvent. Specific examples of the aqueous organic solvent include one or more selected from the group consisting of methanol, ethanol, 1-propanol, 2-propanol, ethyleneglycol, glycerin, acetone, methylethylketone, N,N'-dimethylformamide, N-methylpyrolidone, pyridine, tetrahydrofuran, 1,4-dioxane, acetic acid, acetonitrile, and dimethylsulfoxide. Among these, preferably, methanol, ethanol, 1-propanol, and 2-propanol are used based on the point that these substances are excellent in the easy availability and the industrial productivity such as the drying efficiency and, more preferably, methanol is used based on the point that methanol is especially excellent in the yield.

The amount of the organic solution may be advantageously a 1-fold amount or more by weight, preferably a 3-fold amount or more by weight relative to that of the crude composition of the 4-hydroxy-benzoic acid long chain ester. When the amount of the organic solution is smaller than the 1-fold amount by weight relative to that of the crude composition of the 4-hydroxy-benzoic acid long chain ester, poor stirring may occur in a suspension washing step to be the next step and the purification efficiency tends to be degraded.

In the crystal precipitation step, the organic solution is charged into the container in advance and is stirred. The crude composition of the 4-hydroxy-benzoic acid long chain ester melted at the melting step is added to the organic solution. The process of adding the melted crude composition is not especially limited while, preferably, stepwise addition or addition by instillation may be used to avoid any rapid increase of the temperature. The crude composition may be advantageously set as they are as crystals each having a small particle diameter to block any intake of the catalyst and unreacted carboxylic acid into the inside of each of the crystals. Preferably, the instillation may be conducted at a rate of 5 to 30 g/min.

The pH of the mixed solution of the organic solution and the melted crude composition is adjusted to be 4 to 9, preferably 5 to 8, more preferably 6 to 7. When the pH of the mixed solution is lower than 4, poor stirring tends to occur, and the catalyst and the unreacted carboxylic acid tend to be taken into the crystals because the precipitated crystals tend to be aggregated. When pH thereof is higher than 9, the load of the stirring tends to be increased due to miniaturization of the crystals. As a result, poor stirring tends to occur. In addition, the purification efficiency tends to be degraded.

The organic solution is cooled to the room temperature or lower in advance. When the melted crude composition at the high temperature is added to the organic solution and the suspension washing step is conducted thereafter, the temperature of the mixed solution is maintained at a temperature lower than 45° C., preferably at 5 to 42° C. When the temperature of the mixed solution is 45° C. or higher, it is difficult to take out the crystals because the crystals are dissolved.

In the case where the melted crude composition is added to the mixed solution, when the temperature of the mixed solution is increased to a temperature around 45° C., the temperature is maintained at a temperature lower than 45° C. by temporarily discontinuing the addition of the melted crude composition or by cooling the mixed solution.

The suspension washing step is applied to the crystals obtained in the crystal precipitation step. In the suspension washing step, the stirring is maintained keeping the temperature of the mixed solution in the suspension state where the crystals are precipitated may be maintained at a temperature lower than 45° C. The suspension washing enables removal of the impurities such as the catalyst, the unreacted carboxylic acid, and the like, and purification for the 4-hydroxy-1-benzoic acid long chain ester to have high purity. The suspension washing is advantageously conducted for one hour or longer, preferably for 5 hours or longer.

After the suspension washing step is completed, the crystals may be taken out by solid-liquid separation of the mixed solution such as filtering. In the solid-liquid separation, preferably, washing may be conducted adding water or an organic solvent. Preferably, examples of the organic solvent used in the washing include one or more selected from the group consisting of methanol, ethanol, 1-propanol, and 2-propanol based on the point that these substances are excellent in the easy availability, the yield, and the industrial productivity such as the drying efficiency. The water and the organic solvent to wash the crystals may be advantageously used by a 0.5-fold amount to a 2-fold amount by weight relative to the amount of the crude composition of the 4-hydroxy-benzoic acid long chain ester.

The crystals separated using the solid-liquid separation may be further washed if necessary, and may be dried as they are as crystals under a reduced pressure at a temperature lower than 50° C., or heated to 50° C. or a higher temperature to melt the crystals. Subsequently, the solvent may be distilled away.

As a result, the 4-hydroxy-benzoic acid long chain ester of high purity may be finally acquired.

[Purification Method B]

Firstly, in the dissolving step, the crude composition of the 4-hydroxy-benzoic acid long chain ester may be dissolved in a mixed solution of a non-polar solvent and alcohol.

Examples of the non-polar solvent used in the purification process B include one or more selected from the group consisting of benzene, toluene, o-xylene, m-xylene, p-xylene, ethylbenzene, o-diethylbenzene, m-diethylbenzene, p-diethylbenzene, propylbenzene, cumene, o-cymene, m-cymene, p-cymene, pentane, hexane, heptane, octane, cyclopentane, cyclohexane, cycloheptane, and cyclooctane.

Among these, preferably, toluene, o-xylene, m-xylene, p-xylene, hexane, heptane, octane, and cyclohexane may be used based on the point that these substances are excellent in the safety and the economic efficiency. More preferably, toluene, heptane and hexane may be used based on the point that these substances are especially excellent in the easy availability and the removablity after the recrystallization.

Examples of the alcohol used in the purification process B include one or more selected from the group consisting of methanol, ethanol, 1-propanol, 2-propanol, 1-butanol, 2-butanol, t-butylalcohol, 2-methyl-1-propanol, ethyleneglycol, propyleneglycol, and tetramethyleneglycol.

Among these, preferably, methanol, ethanol, 1-propanol, 2-propanol, and 1-butanol may be used based on the point that these substances are excellent in the safety and the economic efficiency. More preferably, methanol and 2-propanol may be used based on the point that these substances are especially excellent in the easy availability and the removability after the recrystallization.

The ratios of the non-polar solvent and the alcohol may differ depending on the type of the used solvent. Therefore, the ratios of the non-polar solvent and the alcohol are not especially limited. The ratio of the alcohol relative to the mixed solution may be 10 to 90% by weight, preferably 20 to 80% by weight, and more preferably 30 to 70% by weight.

In the purification process B, the ratios of the crude composition of the 4-hydroxy-benzoic acid long chain ester and the mixed solution may be advantageously set for the mixed solution to be a 1.2-fold amount to a 3-fold amount by weight, preferably a 1.5-fold amount to a 2-fold amount by weight relative to the crude composition. When the ratio of the mixed solution is smaller than a 1.2-fold amount by weight relative thereto, the impurities such as the raw materials, the catalyst, and the side products tend to be captured in the crystal and acquisition of highly pure crystals tends to be difficult. When the ratio of the mixed solution is greater than a 3-fold amount by weight relative thereto, the yield of the 4-hydroxy-benzoic acid long chain ester tends to significantly be reduced.

In the dissolving step, the temperature of the mixed solvent of the non-polar solvent and the alcohol may differ depending on the type of the used non-polar solvent and that of the alcohol and the mixing ratios thereof, and is not especially limited. The temperature is preferably 30° C. to 65° C., more preferably 40° C. to 60° C., yet more preferably 45° C. to 55° C.

The crystal precipitation step is applied to the solution having the crude composition dissolved therein.

At the crystal precipitation step, the precipitation is conducted at a temperature of preferably 5 to 30° C., more preferably 5 to 25° C., more preferably 10 to 20° C. with the solution kept being stirred.

When the temperature of the crystal precipitation is lower than 5° C., the impurities such as the raw materials, the catalyst and the side products may be captured in the crystal and acquisition of highly pure crystals becomes difficult. When the temperature of the crystal precipitation is higher than 30° C., the yield of the 4-hydroxy-benzoic acid long chain ester may be reduced.

Solid-liquid separation may be conducted for the crystals precipitated in the crystal precipitation step using a usual process such as filtering to collect the 4-hydroxy-benzoic acid long chain ester which is the target substance. Preferably, after the solid-liquid separation, the crystals may be washed pouring properly the organic solvent thereon. Preferably, one or more selected from the group consisting of methanol, ethanol, 1-propanol, and 2-propanol may be used as the organic solvent used in the solid-liquid separation. Preferably, the organic solvent may be used by a 0.5-fold amount to a 2-fold amount by weight relative to the crude composition of the 4-hydroxy-benzoic acid long chain ester.

The crystals collected using the solid-liquid separation may be dried as they are as crystals under a reduced pressure and at a temperature lower than 50° C., or the crystals may be heated to 50° C. or higher to melt the crystals. After that, the solvent may be distilled away. As a result, the 4-hydroxy-benzoic acid long chain ester of high purity may be obtained.

[Purification Method C]

In the purification process C, firstly, at a dissolving step, the crude composition of the 4-hydroxy-benzoic acid long chain ester may be resolved in an organic solution.

Preferably, the organic solution used in the dissolving step may be a mixture of water and an aqueous organic solvent. Specific examples of the aqueous organic solvent include one or more selected from the group consisting of methanol, ethanol, 1-propanol, 2-propanol, ethyleneglycol, glycerin, acetone, methylethylketone, N,N'-dimethylformamide, N-methylpyrolidone, pyridine, tetrahydrofuran, 1,4-dioxane, acetic acid, acetonitrile, and dimethylsulfoxide. Among these, preferably, methanol, ethanol, 1-propanol, and 2-propanol may be used based on the point that these substances are excellent in the easy availability and the industrial productivity such as the drying efficiency. More preferably, methanol may be used based on the point that methanol is excellent in the yield.

The weight ratio of the water and the aqueous organic solvent (water/the aqueous organic solvent) may be varied depending on the type of the used aqueous organic solvent and may be advantageously 30/70 to 1/99, preferably 20/80 to 2/98, more preferably 15/85 to 3/97. When the ratio of the water and the aqueous organic solvent is higher than 30/70, the 4-hydroxy-benzoic acid long chain ester tends to be difficult to be resolved. When the ratio is lower than 1/99, the yield tends to be reduced.

The amount of the organic solution is not especially limited as far as the crude composition of the 4-hydroxy-benzoic acid long chain ester may be resolved with the amount. The amount may be set to be a 4-fold amount to a 7-fold amount by weight relative to that of the crude composition of the 4-hydroxy-benzoic acid long chain ester. When the amount of the organic solution is smaller than a 4-fold amount by weight relative to that of the crude composition of the 4-hydroxy-benzoic acid long chain ester, the 4-hydroxy-benzoic acid long chain ester tends to be difficult to be resolved. When the amount is larger than the 7-fold amount by weight relative thereto, a long time period tends to be necessary at the next concentration step.

The temperature to dissolve the crude composition of the 4-hydroxy-benzoic acid long chain ester in the organic solution may differ depending on the type of the used organic solution and is not especially limited. Preferably, the temperature may be 50 to 65° C. When the dissolving temperature is lower than 50° C., the crude composition of the 4-hydroxy-benzoic acid long chain ester tends to be difficult to be resolved in the organic solution. When the temperature is higher than 65° C., the crude composition of the 4-hydroxy-benzoic acid long chain ester also tends to be difficult to be dissolved because the organic solution evaporates before the crude composition is dissolved therein to reduce the amount of the organic solution.

A concentration step is applied to the solution containing the crude composition dissolved in the organic solution. The concentration step can be conducted by heating the solution containing the crude composition and/or putting the solution under a reduced pressure to evaporate the organic solution. The heating and the pressure reduction may each be conducted alone or may concurrently be conducted. Preferably, the concentration is conducted by the heating.

The heating temperature may differ depending on the type, the amount, or the concentration of the used organic solution and is therefore not especially limited. The temperature may be preferably 50° C. to 100° C., more preferably 66° C. to 95° C., yet more preferably 70° C. to 90° C.

When the concentration is conducted by the pressure reduction, the pressure during the pressure reduction may differ depending on the type, the amount, or the concentration of the used organic solution and is not especially limited. The concentration may be conducted usually at a pressure of 30 to 50 torr.

The time period of the heating and/or the pressure reduction is not especially limited. Preferably, the heating and/or the pressure reduction may be conducted until the crystals of the 4-hydroxy-benzoic acid long chain ester start to precipitate based on the point that the yield of the 4-hydroxy-benzoic acid long chain ester to be the target substance is improved.

A crystallization step may be applied to the concentrated solution having the crystals starting to precipitate therein at the concentration step.

The crystallization step may be conducted by cooling the concentrated solution. The cooling conditions may differ depending on the type, the amount, or the concentration of the used organic solution and are not especially limited. The cooling may be conducted at 5 to 30° C., preferably 5 to 25° C., more preferably 10 to 20° C. taking 2 to 4 hours. When the cooling temperature is lower than 5° C., the impurities tend also to be crystalized and the purity of the acquired 4-hydroxy-benzoic acid long chain ester tends to be degraded. When the cooling temperature is higher than 30° C., the yield of the 4-hydroxy-benzoic acid long chain ester tends to be reduced.

The crystals precipitated by the cooling may be taken out by solid-liquid separation using filtering and the like. Preferably, in the solid-liquid separation, the crystals may be washed pouring properly an organic solvent thereon. Preferably, one or more selected from the group consisting of methanol, ethanol, 1-propanol, and 2-propanol may be used as the organic solvent used in the solid-liquid separation. Preferably, the organic solvent may be used by a 0.5-fold amount to a 2-fold amount by weight relative to the crude composition of the 4-hydroxy-benzoic acid long chain ester.

The crystals collected using the solid-liquid separation may be dried as they are as crystals under a reduced pressure and at a temperature lower than 50° C., or the crystals may be heated to 50° C. or a higher temperature to melt the crystals. After that, the solvent is thereafter distilled away. As a result, the 4-hydroxy-benzoic acid long chain ester of high purity may be obtained.

The present invention will be described in detail with reference to Examples while the invention is not limited thereto.

EXAMPLES

Conversion Rate and Residual Rate

The mol ratio of the generation amount of each component relative to the charged amount of the aliphatic alcohol was used as the conversion rate. The mol ratio of the residual amount relative to the charged amount of each starting material was used as the residual rate.

The generation amount of each component and the residual amount of each starting material were acquired by quantitative analyses using high-performance liquid chromatography (HPLC) and gas chromatography (GC) under the conditions as below.

[High-Performance Liquid Chromatography (HPLC)]
  Apparatus: Waters Alliance 2487/2996
  Column Model: L-Column
  Liquid Amount: 1.0 mL/min
  Solvent Ratio: $H_2O$ (pH 2.3)/$CH_3OH$=58/42 (30 minutes)→5 minutes→10/90 (55 minutes), gradient analysis
  Wavelength: 229 nm/254 nm
  Column Temperature: 40° C.

[Gas Chromatography (GC)]
  Apparatus: Manufactured by Shimadzu Corporation, GC-2014/GC-14A
  Column Model: G-100
  Injection Amount: 1.0 μL
  Oven Temperature: 310° C.
  Carrier Gas: Helium
  Detector: FID Example 1

179 g of hexadecanol (CeOH) was added into a 1-L four-necked flask including a stirrer, a temperature sensor, and a Dean-and-Stark apparatus, and the temperature thereof was increased up to 70° C. under a gas flow of nitrogen to melt the content. 125 g of methyl 4-hydroxy-benzoate (MOB) and 3.76 g of titanium tetraisopropoxy (TIPT) as a catalyst were added thereto and the temperature of the content was increased up to 160° C. taking one hour to react the content at the same temperature for 6 hours.

Quantitative analyses were conducted for the reaction liquid using the HPLC and the GC. As a result, the conversion rate from the charged CeOH was 96.2 mol % (91.5% by weight) of hexadecyl 4-hydroxy-benzoate (CEPB), and 8.2 mol % (3.5% by weight) of MOB and 2.6 mol % (1.6% by weight) of CeOH remained. No generation was determined for dicetyl ether ($Ce_2O$) which is an ether and hexadecyl-p-toluene-sulfonate (PTS-Ce) which is a sulfate ester.

Comparative Example 1

258 g of CeOH was added into a 1-L four-necked flask including a stirrer, a temperature sensor, and a Dean-and-Stark apparatus, and the temperature thereof was increased up to 70° C. under a gas flow of nitrogen to melt the content. 150 g of 4-hydroxy-benzoic acid (POB), 5.0 g of p-toluene-sulfonic acid monohydrate, and 2.4 g of hypophosphorus acid were added thereto and the temperature of the content was increased up to 130° C. taking one hour to react the content at the same temperature for 8 hours. Quantitative analyses were conducted for the reaction liquid using the HPLC and the GC and, as a result, the conversion rate from the charged CeOH was 92.9 mol % (86.1% by weight) for CEPB, and 8.7 mol % (2.8% by weight) of POB and 3.4 mol % (1.4% by weight) of CeOH remained. The conversion rate of $Ce_2O$ which is an ether was 2.5 mol % (1.8% by weight), and the conversion rate of PTS-Ce which is a sulfate ester was 0.81 mol % (1.0% by weight). Generation of side products was determined.

Example 2

A reaction was conducted similarly to Example 1 except that 263 g of tetracosanol (TcOH) was added as a raw material instead of CeOH. The conversion rate from the charged TcOH was 94.8 mol % (89.1% by weight) of tetracosyl 4-hydroxy-benzoate (TCPB) and, 9.5 mol % (3.9% by weight) of MOB and 3.8 mol % (2.5% by weight) of TcOH remained. No generation was determined for ditetracosyl ether ($Tc_2O$) which is an ether and tetracosyl p-toluene-sulfonate (PTS-Tc) which is a sulfate ester.

Comparative Example 2

A reaction was conducted similarly to Comparative Example 1 except that 347 g of TcOH was added as a raw material instead of CeOH. The conversion rate from the charged TcOH was 92.3 mol % (88.6% by weight) of TCPB and, 9.0 mol % (3.2% by weight) of POB and 3.7 mol % (2.5% by weight) of TcOH remained. The conversion rate of $Tc_2O$ which is an ether was 2.7 mol % (1.8% by weight) and the conversion rate of PTS-Tc which is a sulfate ester was 0.90 mol % (1.0% by weight), and generation of side products was determined.

Example 3

A reaction was conducted similarly to Example 1 except that butyl-4-hydroxy-benzoate (NBE) was added as a raw material instead of MOB. The CEPB conversion rate from the charged CeOH was 70.3 mol %, and 43.8 mol % of NBE and 29.7 mol % of CeOH remained. No generation was determined for $Ce_2O$ which is an ether and PTS-Ce which is a sulfate ester.

Examples 4 to 6

A reaction was conducted similarly to Example 1 except that the amount of CeOH was set to be each of equivalent weights listed in Table 1, that the reaction temperature was set to be 180° C., and that the reaction time period was set to be 4 hours. The results are shown in Table 1.

TABLE 1

| | CeOH Equivalent Amount | Residual Rate (mol %) | | Conversion Rate (mol %) | | |
|---|---|---|---|---|---|---|
| | | MOB | CeOH | CEPB | $Ce_2O$ | PTS-Ce |
| Example 4 | 0.90 | 7.0 | 2.4 | 94.8 | N.D. | N.D. |
| Example 5 | 0.95 | 8.6 | 3.4 | 94.8 | N.D. | N.D. |
| Example 6 | 0.98 | 2.8 | 3.0 | 94.5 | N.D. | N.D. |

MOB: Methyl 4-hydroxy-benzoate
CeOH: Hexadecanol
CEPB: Hexadecyl 4-hydroxy-benzoate
$Ce_2O$: Dicetyl ether
PTS-Ce: Hexadecyl p-toluene-sulfonate
CeOH Equivalent Amount: The mol ratio of the charged amount of CeOH to the raw material MOB
Residual Rate: The mol % of each remaining starting material relative to the charged amount of the starting material
Conversion Rate: The mol % of each generated component relative to the charged amount of CeOH
N.D.: An amount equal to or smaller than the detection limit amount

Examples 7 to 10

A reaction was conducted similarly to Example 1 except that the conditions were set to be those listed in Table 2 concerning the CeOH equivalent weight, the catalyst, the amount of the catalyst, the reaction temperature, and the reaction time period. The results are shown in Table 2 with that of Example 1.

TABLE 2

| | Catalyst | Amount of Catalyst (parts by weight) | CeOH Equivalent Amount | Temperature (° C.) | Time Period (h) |
|---|---|---|---|---|---|
| Example 1 | TIPT | 3 | 0.90 | 160 | 6 |
| Comparative Example 1 | PTS·$H_2O$ | 3 | 0.98 | 130 | 8 |
| Example 7 | MBTO | 3 | 0.98 | 160 | 8 |
| Example 8 | DBTO | 5 | 0.98 | 140 | 8 |
| Example 9 | $Sb(OAc)_3$ | 5 | 0.98 | 180 | 8 |
| Example 10 | $Zr(OBu)_4$ | 5 | 0.98 | 180 | 8 |

| | Residual Rate (mol %) | | Conversion Rate (mol %) | | |
|---|---|---|---|---|---|
| | MOB | CeOH | CEPB | $Ce_2O$ | PTS-Ce |
| Example 1 | 8.2 | 2.6 | 96.2 | N.D. | N.D. |
| Comparative Example 1 | — | 3.4 | 92.9 | 2.5 | 0.81 |
| Example 7 | 5.9 | 2.4 | 96.3 | N.D. | N.D. |
| Example 8 | 9.2 | 2.7 | 96.6 | N.D. | N.D. |
| Example 9 | 6.1 | 2.7 | 95.7 | N.D. | N.D. |
| Example 10 | 4.4 | 4.4 | 93.3 | N.D. | N.D. |

TIPT: Titanium tetraisopropoxide
PTS·$H_2O$: P-toluene-sulfonic acid monohydrate
MBTO: Monobutyl-tin oxide
DBTO: Dibutyl-tin oxide
$Sb(OAc)_3$: Antimony acetate
$Zr(OBu)_4$: Zirconium tetrabutoxide

Examples 11 to 13

A reaction was conducted similarly to Example 1 except that the amount of the catalyst was set to be each of the amounts listed in Table 3. The results thereof are shown in Table 3.

TABLE 3

| | Amount of Catalyst (parts by weight) | Residual Rate (mol %) | | Conversion Rate (mol %) | | |
|---|---|---|---|---|---|---|
| | | MOB | CeOH | CEPB | $Ce_2O$ | PTS-Ce |
| Example 11 | 1 | 10.0 | 3.1 | 96.0 | N.D. | N.D. |
| Example 12 | 2 | 6.8 | 2.2 | 96.3 | N.D. | N.D. |
| Example 13 | 7 | 8.0 | 2.3 | 96.1 | N.D. | N.D. |

Examples 14 to 16

A reaction was conducted similarly to Example 1 except that the reaction temperature was set to be each of the temperatures listed in Table 4. The results thereof are shown in Table 4.

TABLE 4

| | Temperature (° C.) | Residual Rate (mol %) | | Conversion Rate (mol %) | | |
|---|---|---|---|---|---|---|
| | | MOB | CeOH | CEPB | $Ce_2O$ | PTS-Ce |
| Example 14 | 140 | 9.4 | 3.8 | 95.7 | N.D. | N.D. |
| Example 15 | 150 | 8.8 | 2.8 | 96.1 | N.D. | N.D. |
| Example 16 | 170 | 8.2 | 1.9 | 94.8 | N.D. | N.D. |

Example 17 to 19

A reaction was conducted similarly to Example 1 except that the reaction time period was set to be each of the time periods listed in Table 5. The results thereof are shown in Table 5.

TABLE 5

| | Time Period (h) | Residual Rate (mol %) | | Conversion Rate (mol %) | | |
|---|---|---|---|---|---|---|
| | | MOB | CeOH | CEPB | $Ce_2O$ | PTS-Ce |
| Example 17 | 2 | 18.0 | 9.8 | 90.0 | N.D. | N.D. |
| Example 18 | 4 | 11.9 | 4.4 | 94.8 | N.D. | N.D. |
| Example 19 | 8 | 6.3 | 1.7 | 96.7 | N.D. | N.D. |

Example 20

185 g of CeOH was added into a 2-L four-necked flask including a stirrer, a temperature sensor, and a Dean-and-Stark apparatus, and the temperature thereof was increased up to 70° C. under a gas flow of nitrogen to melt the content. 129 g of MOB and 6.5 g of TIPT as a catalyst were added to the above and the temperature of the content was increased up to 150° C. taking one hour to react the content at the same temperature for 8 hours. During this, the flow of nitrogen in the reaction container was set to be 50 ml/min (0.16 ml/min per 1 g of the total amount of MOB and CeOH).

Quantitative analyses were conducted for the reaction liquid obtained using the HPLC and the GC. The results thereof are shown in Table 6.

Example 21

A reaction liquid was acquired similarly to Example 20 except that the flow of nitrogen was set to be 65 ml/min (0.20 ml/min per 1 g of the total amount of MOB and CeOH). Quantitative analyses were conducted for the reaction liquid obtained using the HPLC and the GC. The results thereof are shown in Table 6.

Example 22

A reaction liquid was obtained similarly to Example 20 except that the flow of nitrogen was set to be 97 ml/min (0.30 ml/min per 1 g of the total amount of MOB and CeOH). Quantitative analyses were conducted for the reaction liquid obtained using the HPLC and the GC. The results thereof are shown in Table 6.

Comparative Example 3

A reaction liquid was obtained similarly to Example 20 except that the flow of nitrogen was set to be 16 ml/min (0.05 ml/min per 1 g of the total amount of MOB and CeOH). Quantitative analyses were conducted for the reaction liquid obtained using the HPLC and the GC. The results thereof are shown in Table 6.

Example 23

832 g of CeOH was added into a 2-L four-necked flask including a stirrer, a temperature sensor, and a Dean-and-Stark apparatus, and the temperature thereof was increased up to 70° C. to melt the content. 580 g of MOB and 29.2 g of TIPT as a catalyst were added to the above and the temperature of the content was increased up to 150° C. taking one hour to react the content at the same temperature for 8 hours. During this, the flow of nitrogen in the reaction container was set to be 429 ml/min (0.30 ml/min per 1 g of the total amount of MOB and CeOH).

Quantitative analyses were conducted for the reaction liquid obtained using the HPLC and the GC. The results thereof are shown in Table 6.

Example 24

A reaction liquid was acquired similarly to Example 23 except that a 5-L four-neck flask was used as a reaction container. Quantitative analyses were conducted for the acquired reaction liquid using the HPLC and the GC. The results thereof are shown in Table 6.

Comparative Example 4

A reaction liquid was acquired similarly to Example 23 except that the flow of nitrogen was set to be 71 ml/min (0.65 ml/min per 1 g of the total amount of MOB and CeOH). Quantitative analyses were conducted for the acquired reaction liquid using the HPLC and the GC. The results thereof are shown in Table 6.

Comparative Example 5

A reaction liquid was acquired similarly to Example 23 except that the flow of nitrogen was set to be 923 ml/min (0.65 ml/min per 1 g of the total amount of MOB and CeOH). Quantitative analyses were conducted for the acquired reaction liquid using the HPLC and the GC. The results thereof are shown in Table 6.

TABLE 6

| | | Flow of Nitrogen (ml/min) | | |
|---|---|---|---|---|
| | MOB | Per 1 g of Total Amount of MOB and CeOH | | Reaction Container |
| Example 20 | 129 g | 50 | 0.16 | 2 L |
| Example 21 | 129 g | 65 | 0.20 | 2 L |
| Example 22 | 129 g | 97 | 0.30 | 2 L |
| Comparative Example 3 | 129 g | 16 | 0.05 | 2 L |
| Example 23 | 580 g | 429 | 0.30 | 2 L |
| Example 24 | 580 g | 429 | 0.30 | 5 L |
| Comparative Example 4 | 580 g | 71 | 0.05 | 2 L |
| Comparative Example 5 | 580 g | 923 | 0.65 | 2 L |

| | Residual Rate (mol %) | Conversion Rate (mol %) | |
|---|---|---|---|
| | MOB | CEPB | $Ce_2O$ |
| Example 20 | 12.25 | 90.76 | N.D. |
| Example 21 | 11.31 | 92.07 | N.D. |
| Example 22 | 11.19 | 93.82 | N.D. |
| Comparative Example 3 | 31.66 | 72.89 | N.D. |
| Example 23 | 11.45 | 92.46 | N.D. |
| Example 24 | 11.50 | 92.31 | N.D. |
| Comparative Example 4 | 35.13 | 68.24 | N.D. |
| Comparative Example 5 | 10.83 | 92.19 | 0.28 |

MOB: Methyl 4-hydroxy-benzoate
CEPB: Hexadecyl 4-hydroxy-benzoate
$Ce_2O$: Dicetyl ether
Residual Rate: The mol % of each remaining starting material relative to the charged amount of the starting material
Conversion Rate: The mol % of each generated component relative to the charged amount of CeOH It can be seen as above that, according to the production process of the invention, the 4-hydroxy-benzoic acid long chain ester of high purity may be obtained without generating any side products such as an ether generated by dimerization of the long chain alcohol which is the starting material, a sulfate ester generated by a reaction of the long chain alcohol with the protic acid catalyst, and the like. It can also be seen that, according to the production process of the invention, the reactivity is not degraded even when the scale is increased.

[Crude Composition 1]

179 g of CeOH was added into a 1-L four-necked flask including a stirrer, a temperature sensor, and a Dean-and-Stark apparatus, and the temperature thereof was increased up to 70° C. under a gas flow of nitrogen to melt the content. 125 g of MOB and 3.76 g of TIPT as a catalyst were added to the above and the temperature of the content was increased up to 160° C. taking one hour to react the content at the same temperature for 6 hours. As a result, crude composition 1 was obtained.

Quantitative analyses were conducted for the crude composition 1 using the HPLC and the GC and, as a result, the conversion rate from the charged CeOH was 96.2 mol % for CEPB (91.5% by weight), and 8.2 mol % (3.5% by weight) of MOB and 2.6 mol % (1.6% by weight) of CeOH remained. No generation was determined for $Ce_2O$ which is an ether and PTS-Ce which is a sulfate ester.

[Crude Composition 2]

263 g of TcOH was added into a 1-L four-necked flask including a stirrer, a temperature sensor, and a Dean-and-Stark apparatus, and the temperature thereof was increased up to 70° C. under a gas flow of nitrogen to melt the content.

125 g of MOB and 3.76 g of TIPT as a catalyst were added thereto and the temperature of the content was increased up to 160° C. taking one hour to react the content at the same temperature for 6 hours.

Quantitative analyses were conducted for the crude composition 2 using the HPLC and the GC and, as a result, the conversion rate from the charged TcOH was 94.8 mol % (89.1% by weight) of TCPB, and 9.5 mol % (3.9% by weight) of MOB and 3.8 mol % (2.5% by weight) of TcOH remained. No generation was determined for $Tc_2O$ which is an ether and PTS-Tc which is a sulfate ester.

Example 25

A mixed solution of 372 g of water, 875 g of methanol, and 15 g of phosphoric acid of 85% by weight was charged in a 2-L four-necked flask which had a discharge exit with a cock at its bottom and that included a stirrer, a temperature sensor, and a cooling pipe. 273 g of crude composition 1 was cooled to 110° C. and was thereafter added to the mixed solution. The temperature of the solution was increased up to 60° C. to melt the content and was thereafter stirred at the same temperature for 1 hour. The stirring was stopped and the solution was left untouched at the same temperature for 1 hour. An organic phase and a water phase were thereby separated from each other and the organic phase to be the lower phase was collected through the discharge exit in the bottom.

688 g of methanol was added to the collected organic phase and the temperature of the mixture was again increased up to 60° C. to dissolve the mixture, and the mixture was thereafter cooled to 15° C. to precipitate crystals. The solid matter obtained by the crystal precipitation was taken out using filtering, was washed using 230 g of methanol, and was thereafter dried under the conditions of 45° C. and 10 mmHg to obtain 236 g of crystals.

Quantitative analyses were conducted for the acquired crystals using the HPLC and the GC and, as a result, the purity was 99.4% by weight, the crystals contained 0.2% by weight of CeOH and 0.8% by weight of $CE(PB)_2$, and the content of titanium was 1.2 ppm. No $Ce_2O$ which is an ether and no PTS-Ce which is a sulfate ester were detected.

Comparative Example 6

A mixed solution of 450 g of water, 1,050 g of methanol, and 4.5 g of sodium hydroxide of 48% by weight was charged in a 2-L four-necked flask which had a discharge exit with a cock at its bottom and that included a stirrer, a temperature sensor, and a cooling pipe. 386 g of the crude composition 1 was cooled to 110° C. and was thereafter added to the mixed solution. The temperature of the solution was increased up to 60° C. to melt the content and was thereafter stirred at the same temperature for 1 hour. The stirring was stopped and the solution was left untouched at the same temperature for 1 hour. An organic phase and a water phase were thereby separated from each other.

The organic phase to be the lower layer was collected through the discharge exit in the bottom. 825 g of methanol was added to the collected organic phase and the temperature thereof was again increased up to 60° C. to melt the content. The content was cooled to 15° C. to precipitate crystals. The solid matter acquired by the crystal precipitation was taken out using filtering, was washed using 300 g of methanol, and was thereafter dried under the conditions of 45° C. and 10 mmHg to acquire 352 g of crystals.

Quantitative analyses were conducted for the acquired crystals using the HPLC and the GC and, as a result, the purity was 97.5% by weight, the crystals included 0.2% by weight of CeOH and 1.6% by weight of $CE(PB)_2$, and the content of titanium was 7,300 ppm. Neither $Ce_2O$ which is an ether nor PTS-Ce which is a sulfate ester was detected.

Examples 26 and 27

The same operation was conducted as that of Example 25 except that the weight ratio of water and methanol used in the extraction was set to be each of those listed in Table 7. The liquid separation property was checked, and CEPB was acquired by those whose liquid separation processes were successful. The results are shown in Table 7.

TABLE 7

| Example/Comparative Example | | Example 26 | Example 27 |
|---|---|---|---|
| Water/Methanol Ratio | | 4/6 | 2/8 |
| Liquid Separation Property | | Liquid was able to be separated. | Liquid was able to be separated. |
| CEPB Composition | MOB (% by weight) | 0.03 | 0.01 |
| | CeOH (% by weight) | 0.2 | 0.2 |
| | CEPB (% by weight) | 97.3 | 97.5 |
| | $CE(PB)_2$ (% by weight) | 1.2 | 1.4 |
| | $Ce_2O$ (% by weight) | N.D. | N.D. |
| | POB (% by weight) | N.D. | N.D. |
| | Ti (ppm) | 2.1 | 1.5 |

$CE(PB)_2$: 4-hydroxy-benzoic acid 4-(hexadecyloxycarbonyl)-phenyl ester
$Ce_2O$: Dicetyl ether
POB: 4-hydroxy-benzoic acid
Ti: Titanium Examples 28 to 31

The same operation was conducted as that of Example 25 except that the acid used in the extraction was changed to each of the acids listed in Table 8. The results are shown in Table 8.

TABLE 8

| | | Example 28 | Example 29 | Example 30 | Example 31 |
|---|---|---|---|---|---|
| Acid | | Hydrochloric Acid | Sulfuric Acid | Oxalic Acid | Phosphoric Acid |
| Coloring of Crystal | | Yellowish | Yellowish | Yellowish | Substantially white |
| CEPB Composition | MOB (% by weight) | 0.05 | 0.03 | 0.02 | N.D. |
| | CeOH (% by weight) | 0.4 | 0.3 | 0.3 | 0.2 |
| | CEPB (% by weight) | 98.0 | 97.9 | 98.4 | 98.4 |
| | $CE(PB)_2$ (% by weight) | 1.4 | 1.4 | 1.4 | 1.8 |
| | $Ce_2O$ (% by weight) | N.D. | N.D. | N.D. | N.D. |
| | POB (% by weight) | N.D. | N.D. | N.D. | N.D. |
| | Ti (ppm) | 2.3 | 2.6 | 2.6 | 1.2 |

Examples 32 to 34

The same operation was conducted as that of Example 28 except that the amount of phosphoric acid used in the extraction was set to be each of those listed in Table 9.

TABLE 9

| | | Example 32 | Example 33 | Example 34 |
|---|---|---|---|---|
| | Amount of Phosphoric Acid (% by weight) | 3 | 5 | 10 |
| CEPB Composition | MOB (% by weight) | N.D. | N.D. | N.D. |
| | CeOH (% by weight) | 0.2 | 0.2 | 0.2 |
| | CEPB (% by weight) | 97.1 | 97.5 | 97.9 |
| | CE(PB)$_2$ (% by weight) | 2.0 | 1.8 | 2.0 |
| | Ce$_2$O (% by weight) | N.D. | N.D. | N.D. |
| | POB (% by weight) | N.D. | N.D. | N.D. |
| | Ti (ppm) | 1.1 | 1.2 | 1.2 |

Example 35

A mixed solution of 372 g of water, 875 g of methanol, and 15 g of phosphoric acid of 85% by weight was charged in a 2-L four-necked flask having a discharge exit with a cock at its bottom and including a stirrer, a temperature sensor, and a cooling pipe. 395 g of the crude composition 2 was cooled to 110° C. and was thereafter added to the mixed solution. The temperature of the solution was increased up to 60° C. to melt the content and was thereafter stirred at the same temperature for 1 hour. The stirring was stopped and the solution was left untouched at the same temperature for 1 hour. An organic phase and a water phase were thereby separated from each other. The organic phase to be the lower phase was collected through the discharge exit in the bottom.

688 g of methanol was added to the collected organic phase and the temperature thereof was again increased up to 60° C. to melt the content. The content was thereafter cooled to 15° C. to precipitate crystals. The solid matter acquired by the crystal precipitation was taken out using filtering, was washed using 230 g of methanol, and was thereafter dried under the conditions of 45° C. and 10 mmHg to obtain 349 g of crystals.

Quantitative analyses were conducted for the resulted crystals using the HPLC and the GC and, as a result, the purity was 98.0% by weight, the crystals contained 0.2% by weight of TcOH and 1.5% by weight of Tc(PB)$_2$, and the content of titanium was 1.8 ppm. Neither Tc$_2$O which is an ether nor PTS-Tc which is a sulfate ester was determined.

Comparative Example 7

A mixed solution of 450 g of water, 1,050 g of methanol, and 4.5 g of sodium hydroxide of 48% by weight was charged in a 2-L four-necked bottom-removed flask having a discharge exit with a cock at its bottom and including a stirrer, a temperature sensor, and a cooling pipe. 474 g of the crude composition 2 was cooled to 110° C. and was thereafter added to the mixed solution. The temperature of the solution was increased up to 60° C. to melt the content and was thereafter stirred at the same temperature for 1 hour. The stirring was stopped and the solution was left untouched at the same temperature for 1 hour. An organic phase and a water phase were thereby separated from each other.

The organic phase to be the lower phase was collected through the discharge exit in the bottom. 825 g of methanol was added to the collected organic phase and the temperature thereof was again increased up to 60° C. to dissolve the content. The content was thereafter cooled to 15° C. to precipitate crystals. The solid matter acquired by the crystal precipitation was taken out using filtering, was washed using 300 g of methanol, and was thereafter dried under the conditions of 45° C. and 10 mmHg to obtain 403 g of crystals.

Quantitative analyses were conducted for the acquired crystals using the HPLC and the GC and, as a result, the purity was 97.1% by weight, the crystals contained 0.3% by weight of TcOH and 1.6% by weight of Tc(PB)$_2$, and the content of titanium was 7,800 ppm. Neither Tc$_2$O which is an ether nor PTS-Tc which is a sulfate ester was determined.

As above, according to the purification process of the invention, a 4-hydroxy-benzoic acid long chain ester of high purity can be obtained by adding an acid aqueous solution to a crude composition containing the 4-hydroxy-benzoic acid long chain ester to separate the organic phase and the water phase from each other, and extracting the organic phase.

The invention claimed is:

1. A production process of a 4-hydroxy-benzoic acid long chain ester represented by formula (3), comprising
   a step of reacting a 4-hydroxy-benzoic acid short chain ester represented by formula (1) with an aliphatic alcohol represented by formula (2) in the presence of a metal catalyst to obtain a crude composition containing the 4-hydroxy-benzoic acid long chain ester represented by formula (3),

[Ch. 1]

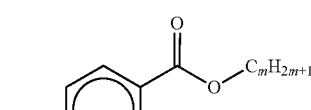

(1)

[Ch. 2]

CH$_3$(CH$_2$)$_n$OH (2)

[Ch. 3]

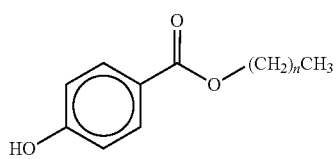

(3)

wherein
"m" represents an integer from 1 to 11 and "n" represents an integer from 15 to 23, and
a step of adding an acid aqueous solution to the crude composition, separating the crude composition to an organic phase and a water phase and extracting the organic phase.

2. The production process according to claim 1, wherein in the step of extracting, a solvent contained in the acid aqueous solution is a mixture of water and a lower alcohol.

3. The production process according to claim 2, wherein the lower alcohol is one or more selected from a group consisting of methanol, ethanol, 1-propanol, and 2-propanol.

4. The production process according to claim 2, wherein a weight ratio of water and the lower alcohol is 5/5 to 2/8.

5. The production process according to claim 1, wherein in the step of extracting, an acid contained in the acid aqueous solution is one or more selected from a group consisting of hydrochloric acid, sulfuric acid, nitric acid, phosphoric acid, carboxylic acid, and sulfonic acid.

6. The production process according to claim 1, wherein a content of the acid in the acid aqueous solution is 0.1 to 10% by weight.

7. The production process according to claim 1, further comprising
a step of precipitating a crystal following addition of an organic solvent to the extracted organic phase.

8. The production process according to claim 7, wherein the organic solvent is methanol.

9. A purification process of a 4-hydroxy-benzoic acid long chain ester, comprising
a step of adding an acid aqueous solution to a crude composition containing the 4-hydroxy-benzoic acid long chain ester represented by formula (3), separating the crude composition to an organic phase and a water phase and extracting the organic phase,

[Ch. 4]

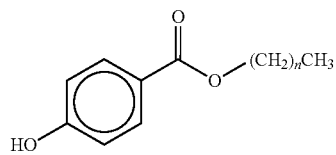

(3)

wherein
"n" represents an integer from 15 to 23.

10. The purification process according to claim 9, wherein in the step of extracting, a solvent contained in the acid aqueous solution is a mixture of water and a lower alcohol.

11. The purification process according to claim 10, wherein
the lower alcohol is one or more selected from a group consisting of methanol, ethanol, 1-propanol, and 2-propanol.

12. The purification process according to claim 10, wherein
a weight ratio of water and the lower alcohol is 5/5 to 2/8.

13. The purification process according to claim 9, wherein in the step of extracting, an acid contained in the acid aqueous solution is one or more selected from a group consisting of hydrochloric acid, sulfuric acid, nitric acid, phosphoric acid, carboxylic acid, and sulfonic acid.

14. The purification process according to claim 9, wherein a content of the acid in the acid aqueous solution is 0.1 to 10% by weight.

15. The purification process according to claim 9, further comprising
a step of precipitating a crystal by adding an organic solvent to the extracted organic phase.

16. The purification process according to claim 15, wherein
the organic solvent is methanol.

17. The production process according to claim 1, wherein the 4-hydroxy-benzoic acid long chain ester represented by formula (3) is hexadecyl 4-hydroxy-benzoate.

18. The production process according to claim 1, wherein the 4-hydroxy-benzoic acid short chain ester represented by formula (1) is methyl 4-hydroxy-benzoate.

19. The production process according to claim 1, wherein 0.1 to 3 mol of the aliphatic alcohol is reacted with 1 mol of the 4-hydroxy-benzoic acid short chain ester.

20. The production process according to claim 1, wherein 0.1 to 10 part(s) by weight of the metal catalyst is present relative to 100 parts by weight of the 4-hydroxy-benzoic acid short chain ester.

21. The production process according to claim 1, wherein the 4-hydroxy-benzoic acid short chain ester and the aliphatic alcohol are reacted at a temperature from 120 to 200° C.

22. The production process according to claim 1, wherein the 4-hydroxy-benzoic acid short chain ester and the aliphatic alcohol are reacted under a gas flow of an inert gas of 0.10 to 0.50 mL/min per 1 g of a total amount of the 4-hydroxy-benzoic acid short chain ester and the aliphatic alcohol.

23. The production process according to claim 22, wherein
the inert gas is one or more selected from a group consisting of nitrogen, carbon dioxide, argon, helium, neon, xenon, and krypton.

24. The production process according to claim 1, wherein the metal catalyst is one or more selected from a group consisting of a titanium-based catalyst, a tin-based catalyst, an antimony-based catalyst, and a zirconium-based catalyst.

* * * * *